United States Patent
Ahn et al.

(10) Patent No.: US 12,360,094 B2
(45) Date of Patent: Jul. 15, 2025

(54) METHOD, APPARATUS AND SYSTEM FOR MONITORING SENSOR HEALTH AND GAS RESPONSE FOR CATALYTIC PELLISTOR POISONING

(71) Applicant: Honeywell International Inc., Charlotte, NC (US)

(72) Inventors: JePhil Ahn, Seoul (KR); Jaeyeol Shim, Seoul (KR); HyungWoo Baek, Seoul (KR); SeungYong Shin, Seoul (KR); WoongSung Hwang, Seoul (KR); HyeonHo So, Seoul (KR); JinEok Cho, Seoul (KR)

(73) Assignee: Honeywell International Inc., Charlotte, NC (US)

( * ) Notice: Subject to any disclaimer, the term of this patent is extended or adjusted under 35 U.S.C. 154(b) by 559 days.

(21) Appl. No.: 17/664,780

(22) Filed: May 24, 2022

(65) Prior Publication Data
US 2023/0384278 A1    Nov. 30, 2023

(51) Int. Cl.
*G01N 33/00*     (2006.01)
*G01N 27/16*     (2006.01)
*G01N 27/417*    (2006.01)

(52) U.S. Cl.
CPC .......... *G01N 33/007* (2013.01); *G01N 27/16* (2013.01); *G01N 27/4175* (2013.01); *G01N 33/0006* (2013.01)

(58) Field of Classification Search
CPC ............. G01N 33/007; G01N 33/0073; G01N 33/0006; G01N 27/16; G01N 27/4175;
(Continued)

(56) References Cited

U.S. PATENT DOCUMENTS

| 7,041,256 B2 | 5/2006 | Wang et al. |
| 2002/0146352 A1 | 10/2002 | Wang et al. |

(Continued)

FOREIGN PATENT DOCUMENTS

| GB | 1550615 A | 8/1979 |
| GB | 2068561 A | 8/1981 |

(Continued)

OTHER PUBLICATIONS

Extended European Search Report Mailed on Oct. 11, 2023 for EP Application No. 23170917, 7 page(s).
(Continued)

*Primary Examiner* — Suman K Nath
(74) *Attorney, Agent, or Firm* — Alston & Bird LLP

(57) ABSTRACT

Methods, apparatuses, and systems for detecting catalytic pellistor poisoning of a gas sensing apparatus including a resistor, a detector, and a compensator are provided. The method includes sampling a voltage reading of the resistor, calculating an electric current value of a gas sensing apparatus circuit based on the sampled voltage reading of the resistor, sampling voltage readings associated with the detector and the compensator for a duration of time, calculating resistance values of the detector and resistance values of the compensator based on the sampled voltage readings from the detector and the compensator, comparing the resistance values of the detector with the resistance values of the compensator, and identifying poisoning of the gas sensing apparatus based on the comparison.

19 Claims, 6 Drawing Sheets

(58) Field of Classification Search
CPC ...... G01N 27/00; G01N 27/222; G01N 27/24; G01N 27/20; G01N 27/223; G01N 27/227
See application file for complete search history.

(56) References Cited

U.S. PATENT DOCUMENTS

| | | | |
|---|---|---|---|
| 2003/0177815 A1 | 9/2003 | White | |
| 2007/0274868 A1* | 11/2007 | Brown | G01N 27/16 422/94 |
| 2008/0034841 A1 | 2/2008 | Bahs et al. | |
| 2012/0318037 A1* | 12/2012 | Lee | G01N 27/16 73/1.06 |

FOREIGN PATENT DOCUMENTS

| | | | |
|---|---|---|---|
| GB | 2332525 A | 6/1999 | |
| WO | 89/11653 A1 | 11/1989 | |

OTHER PUBLICATIONS

Communication about intention to grant a European patent Mailed on Jul. 4, 2024 for EP Application No. 23170917, 6 page(s).
Decision to grant a European patent Mailed on Nov. 7, 2024 for EP Application No. 23170917, 2 page(s).

\* cited by examiner

METHOD, APPARATUS AND SYSTEM FOR MONITORING SENSOR HEALTH AND GAS RESPONSE FOR CATALYTIC PELLISTOR POISONING

FIELD OF THE INVENTION

The present disclosure relates generally to monitoring functionality of gas detectors, and more particularly, to methods, apparatuses, and systems for detecting inoperability of gas detectors having catalytic pellistors.

BACKGROUND

Catalytic pellistor devices are used to detect combustible gases and vapors in the air (for example, in concentrations approaching an explosive range). While catalytic pellistor devices provide fast and accurate gas measurements by exploiting the effects of catalytic reactions, many catalytic pellistor devices are plagued by technical challenges and difficulties.

BRIEF SUMMARY

Various embodiments described herein relate to methods, apparatuses, and systems for monitoring gas detectors. In particular, various embodiments are related to detecting inoperability of a gas sensing device including a detector and a compensator.

In accordance with various examples of the present disclosure, a method is provided for detecting catalytic pellistor poisoning associated with a gas sensing device, wherein the gas sensing device comprises a circuit including a resistor, a compensator, and a detector. The method comprising determining an initial resistor voltage value of the resistor, determining an initial compensator voltage value of the compensator and an initial detector voltage value of the detector, and calculating an initial circuitry current value based at least in part on the initial resistor voltage value and a resistance value of the resistor. Subsequent to causing an injection of a gaseous substance to the gas sensing device, a subsequent compensator voltage value of the compensator and a subsequent detector voltage value of the detector are determined. A subsequent circuitry current value is calculated based on the subsequent resistor voltage value and the resistor resistance value. A compensator resistance change value is calculated based at least in part on the initial circuitry current value, the initial compensator voltage value, the subsequent circuitry current value, and the subsequent compensator voltage value. A detector resistance change value is calculated based at least in part on the initial circuitry current value, the initial detector voltage value, the subsequent circuitry current value, and the subsequent detector voltage value. The method further comprises generating a catalytic pellistor poisoning indicator based at least in part on the compensator resistance change value and the detector resistance change value.

In some embodiments, the initial detector voltage value and the initial compensator voltage value may comprise a baseline reference for establishing functionality of the detector and the compensator. In some embodiments, the baseline reference may be associated with an absence of a gaseous substance. In some embodiments, the initial circuitry current value may comprise an amount of electrical current supplied to the circuit from a supply power source before the injection of the gaseous substance. In some embodiments, calculating the initial circuitry current value may further comprise dividing the initial resistor voltage value by the resistance value of the resistor.

The method may further comprise recording a time of the injection of the gaseous substance and monitoring for changes in the subsequent compensator voltage value and the subsequent detector voltage value. In some embodiments, the subsequent compensator voltage value and the subsequent detector voltage value may correspond to a time after the injection of the gaseous substance. In another embodiment, the method may further comprise executing component failure analysis using the compensator resistance change value and the detector resistance change value.

In some embodiments, generating the catalytic pellistor poisoning indicator may comprise determining that the detector resistance change is analogous to the compensator resistance change subsequent to injection of the gaseous substance. In yet another embodiment, generating the catalytic pellistor poisoning indicator may further comprise determining decreasing detector resistance in conjunction with decreasing compensator resistance subsequent to injection of the gaseous substance. In some embodiments, the detector may comprise a catalytic pellistor including a bead structure with catalytic material. In some embodiments, the compensator may comprise a reference bead structure with non-catalytic material.

According to another embodiment, the method comprises sampling a voltage reading of the resistor and calculating an electric current value of a gas sensing apparatus circuit based on the sampled voltage reading of the resistor. In some embodiments, voltage readings are sampled from the detector and the compensator for a duration of time. In some embodiments, resistance values of the detector and resistance values of the compensator are calculated based on the sampled voltage readings from the detector and the compensator. In some embodiments, the method further comprises comparing the resistance values for the detector with the resistance values for the compensator and identifying poisoning of the gas sensing apparatus based on the comparison.

The method may further comprise calculating the electric current with a resistance value associated with the resistor and the sampled voltage reading of the resistor. In some embodiments, the electric current may be calculated by dividing the sampled voltage of the resistor by the resistance value of the resistor. In some embodiments, the electric current may be provided to the detector and the compensator. In some embodiments, the detector may comprise a catalytic pellistor including a bead structure with catalytic material. In some embodiments, the compensator may comprise a reference bead structure with non-catalytic material. In one embodiment, calculating resistance values of the detector and resistance values of the compensator further comprises dividing the sampled voltage readings from the detector and the compensator by the electric current.

According to another embodiment, a system is provided for detecting catalytic pellistor poisoning of a gas sensing apparatus including a resistor, a detector, and a compensator. The system comprises a memory device having executable instructions stored therein and a processor. In response to the executable instructions, the processor is configured to sample a voltage reading of the resistor and calculate electric current of a gas sensing apparatus circuit based on the sampled voltage reading of the resistor. The processor is further configured to sample voltage readings of the detector and the compensator for a duration of time and calculate resistance values for the detector and resistance values for the compensator based on the sampled voltage readings of the detector and the compensator. The processor is further configured to compare the resistance values of the detector with the resistance values of the compensator and identify poisoning of the gas sensing apparatus based on the comparison.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein.

DETAILED DESCRIPTION OF THE INVENTION

Figure 1:
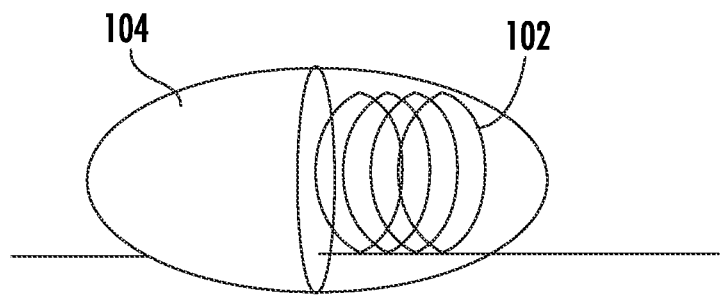
FIG. 1 illustrates a half cross-sectional view of an exemplary bead structure in accordance with various embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The phrases "in one embodiment," "according to one embodiment," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such component or feature may be optionally included in some embodiments, or it may be excluded.

As described above, many catalytic pellistor devices are plagued by technical challenges and difficulties. Such devices may include a pellistor comprising a small ceramic bead cast on a coil or wires. The pellistor may include a catalyst surface and function as a heater and/or a thermometer. At an appropriate temperature, the catalyst surface causes a gaseous substance (such as a gas or vapor) to be measured by the catalytic pellistor devices reacts (e.g., combusts) with oxygen from the air. Heat produced by this reaction increases the temperature of the bead and an electrical resistance of the coil or wires. The change in resistance provides a measurement of the amount of combustible gas or vapor.

Despite their usefulness, catalytic pellistors are susceptible to poisoning, which may cause loss of sensitivity or inoperability. In the present disclosure, the terms "poisoning" or "catalytic poisoning" may refer to a decrease or loss of the pellistor's sensitivity due to deposits, debris, residues, contaminant, and/or substances that accumulate and remain on the catalyst surface of the catalytic pellistor. For example, compounds containing silicon or other adsorbent materials on the catalyst surface may impair a catalytic pellistor's gas reaction, resulting in reduced performance or failure. Catalytic poisoning is a costly problem as it can decrease the accuracy of sensor readings and destroy the usefulness of expensive catalyst systems used in gas detection.

Catalytic pellistor devices may be inspected prior to use for ensuring correct operation. For example, a controlled concentration of flammable gas may be introduced across a detector of a catalytic pellistor and monitored for an expected response (e.g., ignition and/or alarm). If the detector fails the testing condition and does not provide the expected response, the catalytic pellistor may be determined to be malfunctioning. For such testing to be effective, it should be performed regularly or as part of a maintenance schedule, which can be time consuming, expensive, and cumbersome. However, poisoning of a catalytic pellistor may occur in between inspections. For example, when an inspection identifies that a catalytic pellistor device has been malfunctioning due to poisoning, the catalytic pellistor device may have already been inoperable for a period time. The delay between the time that the catalytic pellistor device is poisoned and the time that the poisoning is identified can cause safety hazards.

Thus, there is a need for a catalytic pellistor monitoring system that provides real-time detection of malfunctioning catalytic pellistor components due to poisoning.

In accordance with various examples of the present disclosure, a catalytic pellistor may include a detector comprising catalyst-load ceramic that is sensitive to combustible gases, and a compensator which is inert. When in operation, combustible gas may be burned by the detector, causing a rise in its temperature and resistance. Heat generated from the burning can measured by the detector. Meanwhile, the compensator does not burn the combustible gas and its temperature and resistance remains unchanged or reduced in the presence of combustible gases. The compensator may provide an inactive reference to compensate for environmental factors, such as temperature and pressure. For example, temperature measured by the detector may be compared with temperature of the compensator.

In accordance with various examples of the present disclosure, a compensator and/or a detector may be in various forms. In some embodiments, the compensator and/or the detector may be in the form of a bead structure. Referring now to FIG. 1, an example bead structure is shown. In particular, FIG. 1 provides a half cross-sectional view of an exemplary bead structure according to various embodiments disclosed herein. A metal wire coil 102 is disposed within a cover member 104.

In some embodiments, an example gas sensing apparatus may comprise two bead members. A first of the bead structures (the "detector") may include cover member 104 that comprises catalytic material. The catalytic material may allow catalytic combustion or oxidation to occur. In this regard, when a voltage is supplied to the metal wire coil 102, the metal wire coil 102 may heat the bead member. When the voltage is high enough, the high temperature of the bead structure may cause the combustible gaseous substance to react on the detector (e.g., catalytic oxidation).

A second of the bead structures (the "compensator") may include cover member 104 that comprises non-catalytic material, and may resemble the detector in other respects. In other words, the compensator does not trigger catalytic combustion or oxidation, and the combustible gaseous substance may remain inert on the compensator.

Figure 2:
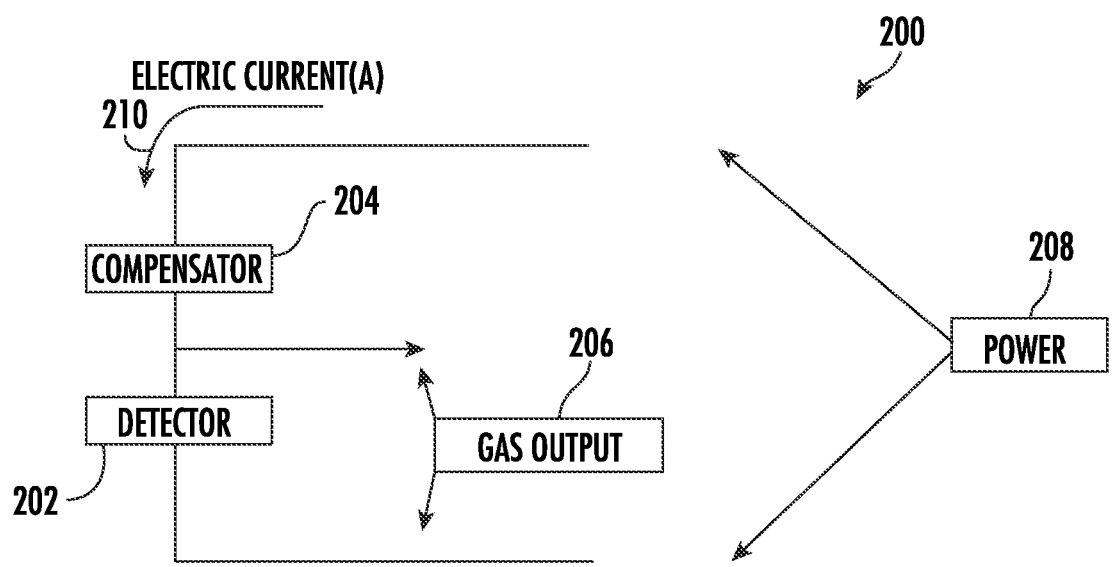
FIG. 2 illustrates an example diagram of various components of an example gas sensing apparatus in accordance with various embodiments of the present disclosure.

Referring to FIG. 2, a schematic of a gas sensing apparatus 200 is provided, which may be used in accordance with various embodiments of the present disclosure. Gas sensing apparatus 200 comprises a gas sensing apparatus circuit including a detector 202 comprising a catalytic pellistor (e.g., bead structure with catalytic material) and a compensator 204 (e.g., bead structure with non-catalytic material) that are configured based on a bridge circuit (e.g., Wheatstone bridge circuit). The gas sensing apparatus 200 is supplied with an electric current 210 via power source 208.

The metal wire coil of detector 202 may have an electrical resistance of $R_D$, and the metal wire coil of the compensator 204 may have an electrical resistance of $R_c$. During normal operation in a non-poisoned state of gas sensing apparatus 200, when combustible gases are present, a catalytic reaction may occur at detector 202, which causes a rise in both temperature and electrical resistance $R_D$ associated with the detector 202. Meanwhile, temperature and electrical resistance of $R_c$ associated with compensator 204 may remain constant or slightly lower due to a loss of heat carried away by gas via gas thermal conductivity phenomenon. The rise and change in resistance $R_D$ of the detector 202 may create an imbalance in the circuit. That is, a difference between electrical resistance $R_D$ and electrical resistance of $R_c$ may be measured across the detector 202 as a gas output signal 206. Gas output signal 206 may comprise a value that is proportional to a concentration of combustible gas being detected. As such, the gas concentration can be determined based on the resistance $R_D$ of the detector 202.

In the event of mild poisoning of the gas sensing apparatus 200, functionality (e.g., catalytic reaction) of detector 202 may be reduced, causing a reduction in temperature increase and a reduction in increase of electrical resistance $R_D$, resulting in gas output signal 206 to be inaccurate or inconsistent with the concentration of combustible gas (relative to normal operation). In the case of extreme poisoning, functionality of detector 202 may be faulty or non-existent, thereby causing no increase in temperature or electrical resistance of $R_D$ and producing an erroneous gas output signal 206 representative of no gas being detected. In such a case, despite the compensator 204 being exposed to gas, the compensator 204 does not react with the gas, and the state of the gas sensing apparatus 200 electrically corresponds to a state when there is zero gas. Thus, extremely poisoned gas sensing apparatus 200 cannot be used as intended (e.g., as a safety device).

Figure 3:
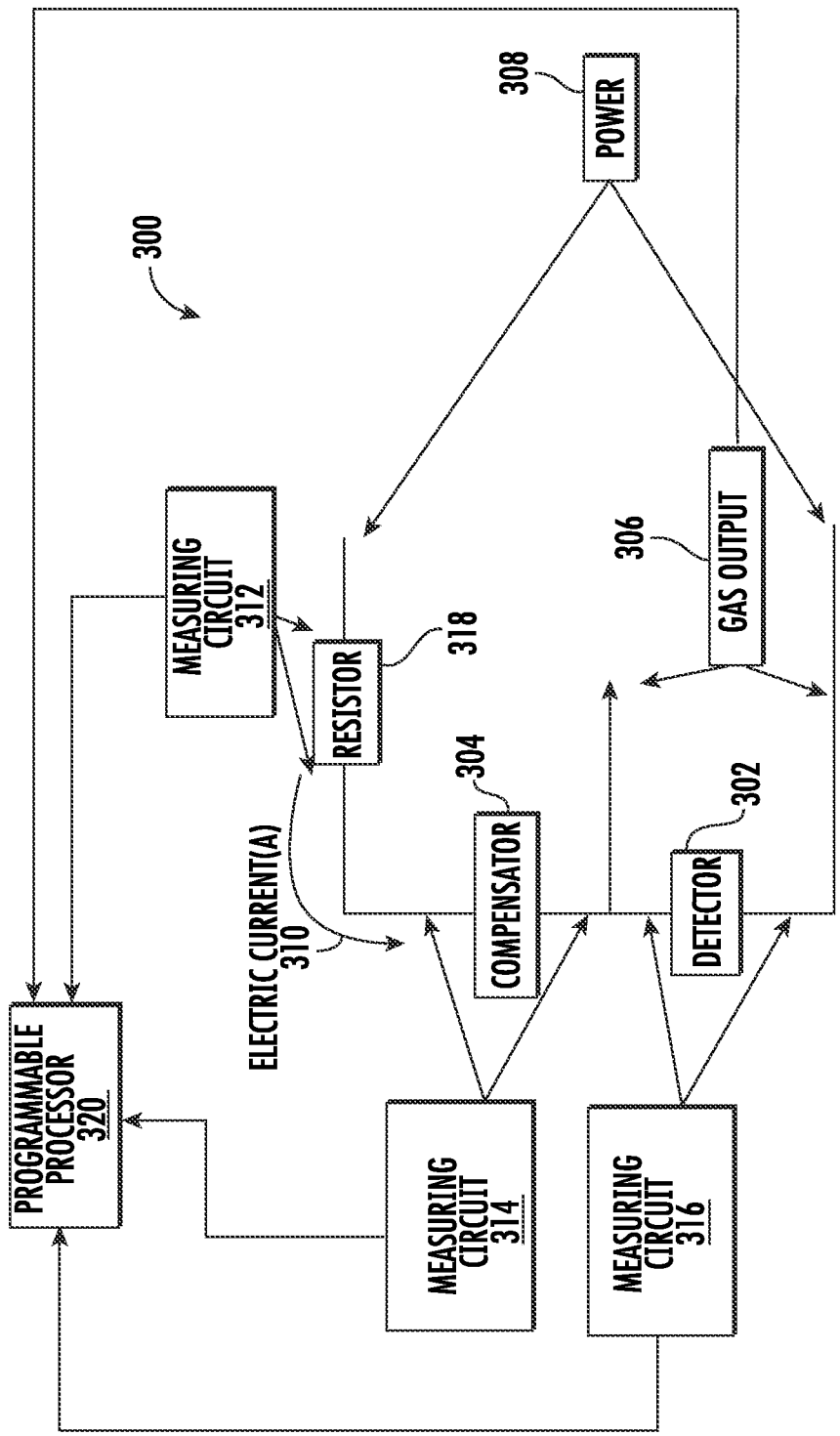
FIG. 3 illustrates an example diagram of various components of an example gas sensing circuitry in accordance with various embodiments of the present disclosure.

According to various embodiments of the present disclosure, a gas sensing apparatus may be modified for monitoring of catalytic pellistor poisoning by adding a resistor to the gas sensing apparatus circuit and connecting measuring circuitry to metal wire coils of bead members and to the resistor. Referring to FIG. 3, a schematic of a gas sensing apparatus 300 is provided which may be used in accordance with various embodiments of the present disclosure. Gas sensing apparatus 300 comprises a bridge circuit portion including a detector 302 comprising a catalytic pellistor (e.g., bead structure with catalytic material) and a compensator 304 (e.g., bead structure with non-catalytic material). For example, a first lead of the detector 302 is directly coupled to a first lead of the compensator 304. The gas sensing apparatus 300 further comprises a resistor 318 connected in series to the compensator 304 (for example, a first lead of the resistor 318 is directly coupled to a second lead of the compensator 304). A power source 308 is directly coupled to both the resistor 318 (for example, a second lead of the resistor 318) and the bridge circuit portion (for example, a second lead of the detector 302). As such, electric current flows from the power source 308 to the second lead of the resistor 318 and through the resistor 318, from the first lead of the resistor 318 to the second lead of the compensator 304 and through the compensator 304, from the first end of the compensator 304 to the first end of the detector 302 and through the detector 302, and from the second end of the detector 302 to the power source 308.

Gas sensing apparatus 300 further comprises measuring circuit 312, measuring circuit 314, and measuring circuit 316. The metal wire coil of detector 302 may have an electrical resistance of $R_D$, and the metal wire coil of the compensator 304 may have an electrical resistance of $R_c$. During normal operation of the gas sensing apparatus 300, the values of electrical resistance of $R_D$ and electrical resistance of $R_c$ may have a same resistance value during a steady state (e.g., when no gas is present). However, in cases of poisoning of the gas sensing apparatus 300, measuring values of $R_D$ and $R_c$ may be used to detect malfunctioning of at least the detector 302 according to various embodiments of the present disclosure. In some embodiments, resistor 318 may comprise a shunt resistor including a fixed value resistor. Additionally, or alternatively, resistor 318 may comprise a variable resistor, such as a potentiometer. Accordingly, the resistance value of resistor 318 may be provided, e.g., via manual input or digitally programmed/preconfigured, to programmable processor 320.

Measuring circuit 312 is configured in parallel with resistor 318. The measuring circuit 312 may comprise a voltage meter that comprises any combination of at least one of leads, contacts, and probes. For example, a first lead of the measuring circuit 312 (e.g., a voltage meter) is directly coupled to the circuit wire between the power source 308 and the second lead of the resistor 318, and a second lead of the measuring circuit 312 (e.g. the voltage meter) is directly coupled to the circuit wire between the first lead of the resistor 318 and the second lead of the compensator 304. In some embodiments, the measuring circuit (e.g. the voltage meter) is further coupled to a programmable processor 320. The programmable processor 320 may be configured to calculate electric current 310 by measuring a voltage drop across resistor 318 using measuring circuit 312 and applying, e.g., Ohm's law (voltage=electric current×resistance) with the known resistance value of resistor 318. The calculated electric current 310 is provided to detector 302 and compensator 304 in the series connection. As such, values of $R_D$ and $R_c$ may be calculated (e.g., Ohm's law) by programmable processor 320 using the calculated electric current 310 and voltage measurements of the detector 302 via measuring circuit 316 and of the compensator 304 via measuring circuit 314. For example, measuring circuit 314 is configured in parallel with compensator 304 and measuring circuit 316 is configured in parallel with detector 302. The measuring circuit 314 and measuring circuit 316 may each comprise any combination of at least one of leads, contacts, and probes coupled to a voltage meter (not illustrated) and coupled to the programmable processor 320. For example, a first lead of the measuring circuit 314 (e.g. a voltage meter) is directly coupled to the circuit wire between the first lead of the resistor 318 and the second lead of the compensator 304, and a second lead of the measuring circuit 314 (e.g. the voltage meter) is directly coupled to the circuit wire between the first lead of the compensator 304 and the first lead of the detector 302. Similarly, a first lead of the measuring circuit 316 (e.g. a voltage meter) is directly coupled to the circuit wire between the first lead of the compensator 304 and the first lead of the detector 302, and a second lead of the measuring circuit 316 (e.g. the voltage meter) is directly coupled to the circuit wire between the second lead of the detector 302 and the power source 306. That is, a voltage measured across detector 302 and the calculated electric current 310 may be used by programmable processor 320 to calculate $R_D$. Similarly, a voltage measured across compensator 304 and the calculated electric current 310 may be used by the programmable processor 320 to calculate $R_c$.

Resistance values of the detector 302 and compensator 304 may be monitored by programmable processor 320 during operation of gas sensing apparatus 300. The programmable processor 320 may be implemented as, for example, various devices comprising one or a plurality of microprocessors with accompanying digital signal processors; one or a plurality of processors without accompanying digital signal processors; one or a plurality of coprocessors; one or a plurality of multi-core processors; one or a plurality of controllers; processing circuits; one or a plurality of computers; and various other processing elements (including integrated circuits, such as ASICs or FPGAs, or a certain combination thereof). In some embodiments, the programmable processor 320 may comprise one or more processors.

The programmable processor 320 may be configured to recognize that, during normal operation and in a non-poisoned state of gas sensing apparatus 300, the resistance value $R_D$ of detector 302 may increase in reaction to gas (e.g., caused by a catalytic reaction). The increase in resistance value $R_D$ of detector 302 may be confirmed with a higher gas output 306 reading to confirm that a normal gas reaction is occurring. Various gas output 306 and resistance value $R_D$ for a non-poisoned state may be stored to establish baseline functionality of gas sensing apparatus 300. Furthermore, the programmable processor 320 may also be configured to account for loss of heat carried away by gas due to gas thermal conductivity phenomenon, which may cause the resistance value $R_c$ of compensator 304 to decrease due to loss of heat carried away by gas due to gas thermal conductivity phenomenon. Gas thermal conductivity phenomenon may also cause the resistance value $R_D$ of detector 302 to decrease, particularly when detector 302 is poisoned and does not react to the gas. However, the decrease in the resistance value $R_D$ of detector 302 due to gas thermal conductivity may be offset by the increase in the resistance value $R_D$ of detector 302 due to heat produced by a reaction to gas by the detector 302, particularly when detector 302 is not poisoned. As such, resistance values corresponding to the detector 302 and the compensator 304 may be used by the programmable processor 320 to determine if the detector 302 is poisoned while exposed to gas.

According to one embodiment, poisoning state of the detector 302 may be confirmed by the programmable processor 320 by checking the resistance of compensator 304. For example, when the detector 302 is exposed to gas, the programmable processor 320 may detect a decrease in resistance value $R_D$ and a decrease in resistance value $R_c$, indicating that detector 302 is not catalytically reacting to the gas, and both detector 302 and compensator 304 are experiencing loss of heat by introduction of the gas. Programmable processor 320 may also identify reduced function of detector 302 when exposed to gas due to mild poisoning. That is, the programmable processor 320 may compare readings of gas output 306, resistance value $R_D$, and resistance value $R_c$ with the baseline functionality discussed above. Resistance value $R_D$ for a given gas output reading that is lower than a baseline resistance value $R_D$ for the same given gas output value may indicate reduced reaction of detector 302 to the gas, and mild poisoning of the detector 302. According to another embodiment, detector functionality may be measured based on a ratio of power at the detector 302 (e.g., power=current×voltage) to resistance value $R_D$.

Figure 4:
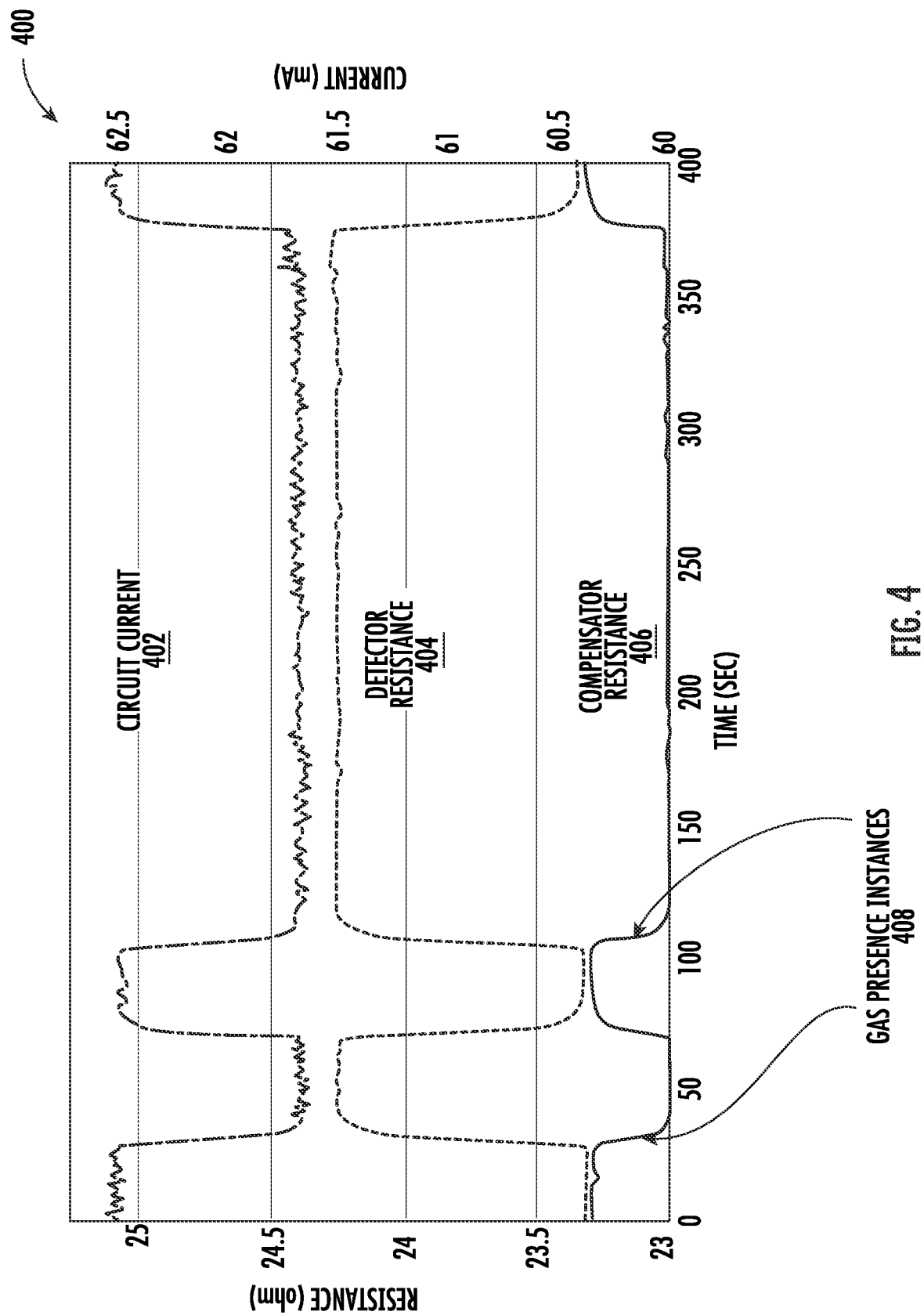
FIG. 4 illustrates measurement readings associated with normal operation of a gas sensing apparatus according to operations performed by a computing device in accordance with various embodiments described herewith.

FIG. 4 presents measurement readings associated with normal operation of a gas sensing apparatus according to the operations performed by a computing device in accordance with various embodiments described herewith. A computing device, for example, comprising programmable processor 320, may receive or sample signals from measuring circuits 312, 314, and 316 of gas sensing apparatus 300. The computing device may process the signals and generate data readings for a monitoring user interface 400. Monitoring user interface 400 includes a circuit current channel 402, a detector resistance channel 404, and a compensator resistance channel 406. The circuit current channel 402 may correspond to an electric current calculated for the gas sensing apparatus 300 (e.g., calculated electric current 310) using techniques described herein. The detector resistance channel 404 and the compensator resistance channel 406 may correspond to calculated resistance values for detector 302 and compensator 304, respectively, also as discussed herein. Data readings associated with channels 402, 404, and 406 are plotted along a horizontal time axis measured in seconds, and dual vertical axes including resistance measured in ohms and electrical current measured in milliamperes (mA).

According to the illustrated embodiment, the data values presented in monitoring user interface 400 may correspond to a baseline for comparison with poisoning conditions. For example, data readings associated with channels 402, 404, and 406 may be recorded during testing or calibration of gas sensing apparatus with gas. The recorded data may be used to create a reference or, in other embodiments, training data for machine learning, corresponding to normal operation of gas sensing apparatus 300. In one embodiment, supervised learning is employed to create training data by associating data readings of channels 402, 404, and 406 to normal functionality of a gas sensing apparatus during no gas presence and during gas presence. The training data may then be used by a computing device to infer a function based on the training data to create an event classifier configured to detect normal and abnormal functionality of the gas sensing apparatus.

Gas presence instances 408 correspond to certain time periods where gas is injected (e.g., 50% Lower Explosive Limit (LEL)) into a system monitored by gas sensing apparatus 300. When gas is injected during gas presence instances 408, detector resistance channel 404 indicates significantly increased resistance values of the detector. Meanwhile, circuit current channel 402 indicates decreased current readings and compensator resistance channel 406 indicates lower resistance values during the gas presence instances 408.

Gas sensing apparatus 300 is provided with a constant voltage during operation. The increased resistance of the detector, as indicated by detector resistance channel 404, being larger than the decrease in resistance of the compensator, as indicated by compensator resistance channel 406, causes an increase in the resistance/electrical impedance of the gas sensing apparatus circuit of the gas sensing apparatus 300. As a result of the increased resistance/electrical impedance, the electric current 310, as indicated by circuit current channel 402, is reduced.

Figure 5:
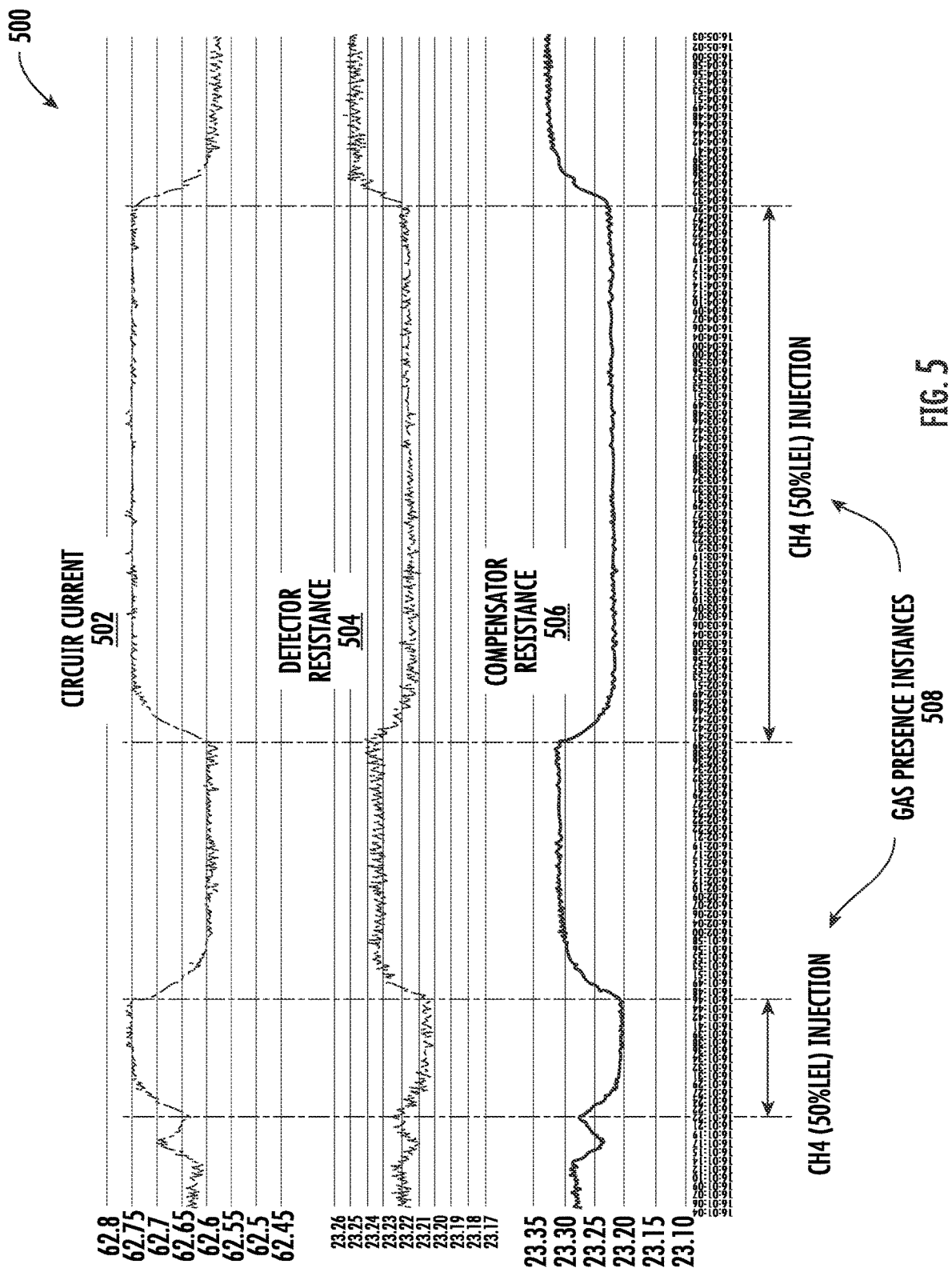
FIG. 5 illustrates measurement readings associated with poisoning of a gas sensing apparatus according to operations performed by a computing device in accordance with various embodiments described herewith

FIG. 5 presents measurement readings when a gas sensing apparatus is poisoned according to the operations performed by a computing device in accordance with various embodiments described herewith. According to the illustrated embodiment, the data values presented in monitoring user interface 500 may correspond to detection of a same or similar concentration of gas, as discussed with respect to FIG. 4, but in a scenario where the gas sensing apparatus 300 has been poisoned by a contaminant, e.g., silicon. A computing device, for example, comprising programmable processor 320, may generate data readings for the monitoring user interface 500 based on signals received or sampled from measuring circuits 312, 314, and 316 of gas sensing apparatus 300.

Monitoring user interface 500 includes a circuit current channel 502, a detector resistance channel 504, and a compensator resistance channel 506. The circuit current channel 502 may correspond to an electric current calculated for the gas sensing apparatus 300 (e.g., calculated electric current 310), as discussed herein. The detector resistance channel 504 and the compensator resistance channel 506 may correspond to calculated resistance values for detector 302 and compensator 304, respectively, also as discussed herein. Data readings associated with channels 502, 504, and 506 are plotted along a horizontal time axis measured in seconds, and dual vertical axes including resistance measured in ohms and electrical current measured in milliamperes (mA).

In the case of poisoning, detector resistance channel 504 indicates resistance values that are lower than the baseline, especially when gas in injected during gas presence instances 508. Particularly, detector resistance channel 504 indicates no detection or catalytic reaction to gas during gas presence instances 508. Instead, both detector resistance channel 504 and compensator resistance channel 506 indicate decreases in resistance, e.g., due to loss of heat from gas thermal conductivity. The decreases in resistance of both detector 302 and compensator 304 may cause the resistance/electrical impedance of the gas sensing apparatus circuit of the gas sensing apparatus 300 to decrease (and the electric current 310 to increase in an example where a constant voltage is applied to the circuit) when gas in injected during gas presence instances 508, as indicated by circuit current channel 502. Accordingly, an increase in circuit current channel 502 reading in combination with decreases in detector resistance channel 504 and compensator resistance channel 506 may be indicative of poisoning of detector 302.

Additionally, or alternatively, by monitoring the compensator resistance channel 506 in relationship to the circuit current channel 502, or compensator resistance per wattage of power (e.g., power=electric current×voltage), poisoning and reduced functionality of detector 302 may be detected and a gas alarm can be issued regardless of the value of detector resistance channel 504. Resistance value per power ratio may be used as a metric for determining detector functionality based on a circuit imbalance (e.g., of the bridge circuit) as a result of lower-than-normal resistance of detector 302. For example, a decrease in gas output detection due to partial poisoning, can be detected by a computing device by calculating a real-time resistance value per power ratio of the compensator 304 and comparing it with a baseline/historical resistance value per power ratio of the compensator 304. A real-time resistance value per power ratio of the compensator 304 that is lower than the baseline/historical resistance value per power ratio of the compensator 304 may indicate partial positioning.

Figure 6:
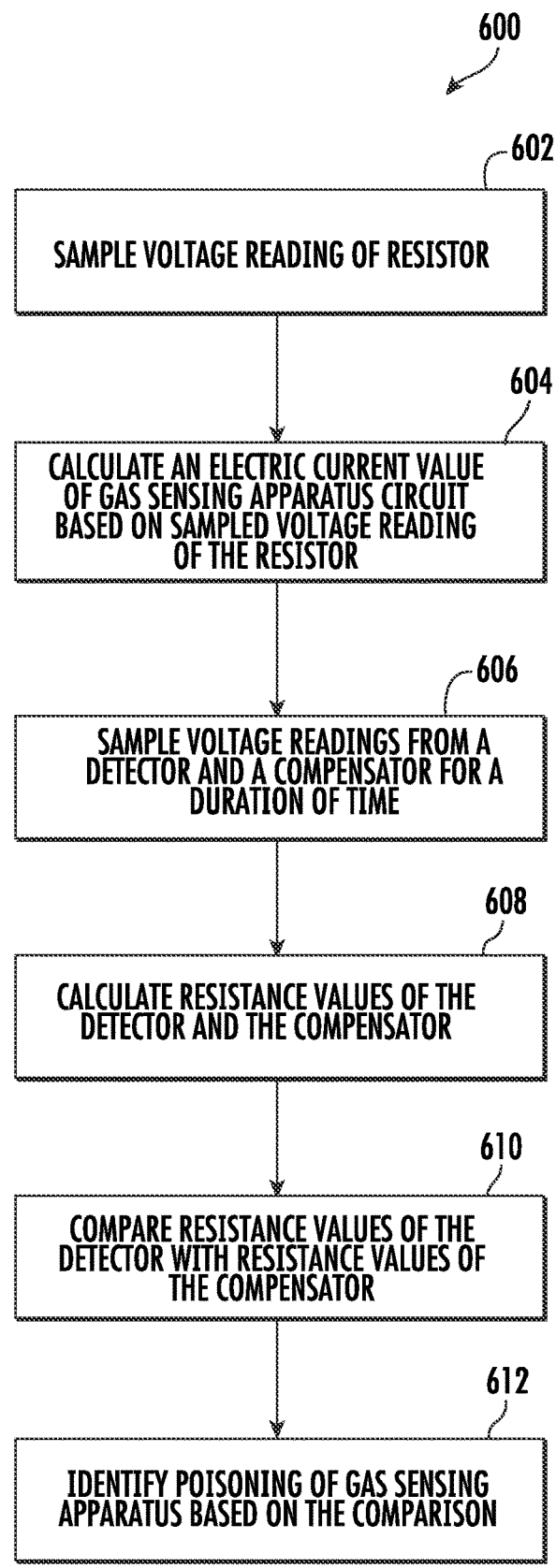
FIG. 6 illustrates an example method executed by a computing device associated with a gas sensing apparatus in accordance with various embodiments of the present disclosure.
Figure 7:
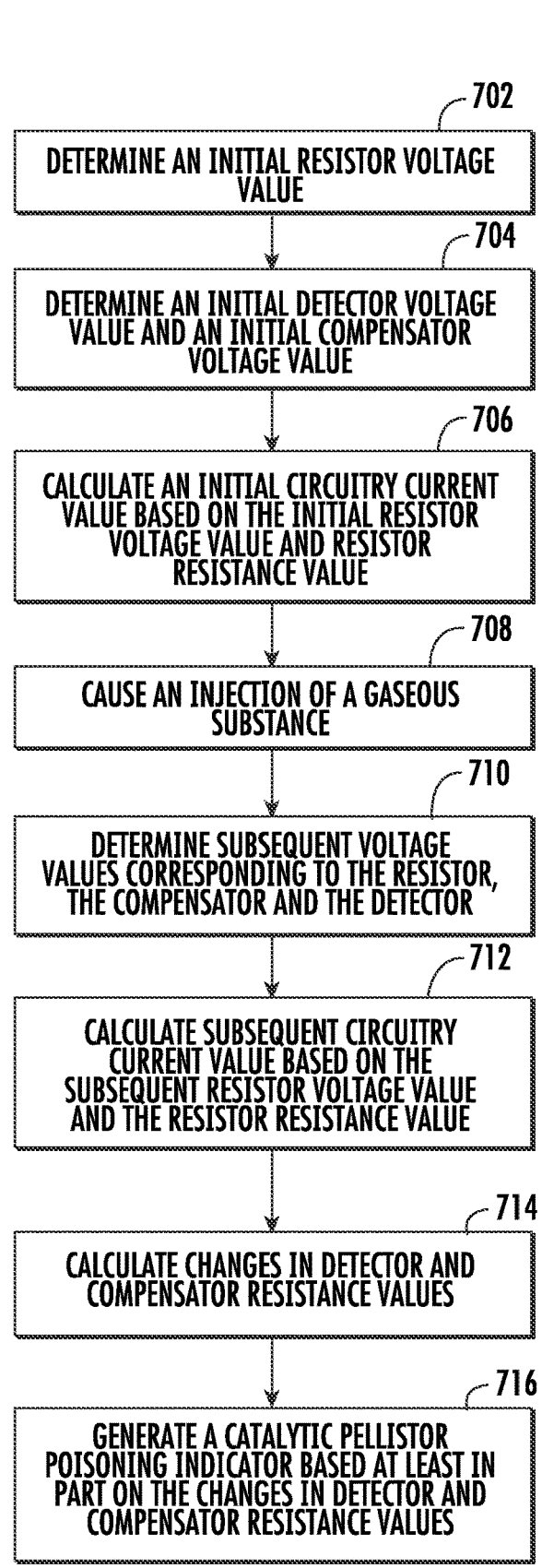
FIG. 7 illustrates an example flowchart for testing a gas sensing apparatus in accordance with various embodiments of the present disclosure.

Referring now to FIG. 6 and FIG. 7, example flow diagrams illustrating exemplary methods of detecting catalytic pellistor poisoning in accordance with some example embodiments of the present disclosure are provided. It is noted that each block of a flowchart, and combinations of blocks in the flowchart, may be implemented by various means such as hardware, firmware, circuitry and/or other devices associated with execution of software including one or more computer program instructions. For example, one or more of the steps/operations described in FIG. 6 and FIG. 7 may be embodied by computer program instructions, which may be stored by a non-transitory memory of an apparatus employing an embodiment of the present disclosure and executed by a processor component in an apparatus (such as, but not limited to, a gas sensing apparatus, a programmable processor, a client computing device, a remote computing server, and/or the like). For example, these computer program instructions may direct the processor component to function in a particular manner, such that the instructions stored in the computer-readable storage memory produce an article of manufacture, the execution of which implements the function specified in the flowchart block(s).

In FIG. 6, the example method 600 may be executed by a computing device associated with a gas sensing apparatus including a detector, a compensator, and a resistor (for example, as illustrated and described above in connection with at least FIG. 3). At step 602, voltage reading of a resistor is sampled from a first measuring circuit. The first measuring circuit may comprise any one of leads, probes, and contacts configured in parallel with the resistor for measuring voltage by a voltage meter coupled to the computing device.

In some embodiments, subsequent to step 602, the example method proceeds to step 604, where electric current of the gas sensing apparatus circuit of the gas sensing apparatus is calculated based on the sampled voltage reading of the resistor. The computing device may be configured to calculate the electric current by applying, for example, Ohm's law with a resistance value of the resistor and the sampled voltage of the resistor. The resistance value of the resistor may be a known or preconfigured resistance value that can be set as a programmable variable on the computing device. The electric current may be calculated by the computing device by dividing the sampled voltage of the resistor by the resistance value of the resistor. The calculated electric current may be representative of electric current provided to both the detector and the compensator.

In some embodiments, subsequent to step 604, the example method proceeds to step 606, where voltage readings associated with a detector and from a compensator are sampled for a duration of time. Sampling voltage readings associated with the detector may comprise receiving signal readings from a second measuring circuit coupled to the detector. Sampling voltage readings associate with the compensator may comprise receiving signal readings from a third measuring circuit coupled to the compensator. The second and third measuring circuits may comprise any one of leads, probes, and contacts configured in parallel with the detector and the compensator, respectively, for measuring voltages by voltage meters in communication with the computing device. The detector may comprise a catalytic pellistor including a bead structure with catalytic material. The compensator may comprise a reference bead structure with non-catalytic material, and the compensator is used in conjunction with the detector. The sampled voltage readings of the detector and the compensator may be used to calculate resistance values for the detector and the compensator, respectively.

In some embodiments, subsequent to step 606, the example method proceeds to step 608, where resistance values of the detector and the compensator are calculated based on the sampled voltage readings from the detector and the compensator. The computing device may calculate resistance values for the detector and resistance values for the compensator by, for example, dividing the respective sampled voltage readings of the detector and the compensator by the calculated electric current.

In some embodiments, subsequent to step 608, the example method proceeds to step 610, where resistance values of the detector are compared with resistance values of the compensator. The resistance values of the detector and the compensator may be indicative of their functionality. That is, the resistance values between the detector and the compensator may be compared to provide an indication of detector poisoning and overall functionality of the gas sensing apparatus. As described above, the resistance value of the detector and the resistance value of the compensator are the same when the gas sensing apparatus is not in use (e.g., when the gas is not injected to the gas sensing apparatus). When the gas sensing apparatus operates under normal condition (e.g., when there is no poisoning), resistance values of the detector may increase in the presence of a gas due to a catalytic reaction of the detector with the gas, while resistance values for the compensator decrease due to loss of heat from gas thermal conductivity. However, when the detector is poisoned, catalytic reaction to gas may be reduced, which reduces the amount of increase (or causes no increase, or a decrease due to loss of heat from gas thermal conductivity) in the resistance values of the detector, while resistance values for the compensator decrease due to loss of heat from gas thermal conductivity. In the case of extreme poisoning of the detector, catalytic reaction to gas may be non-existent and the resistance value of the detector may instead mirror a decrease in the resistance value of the compensator where both detector and compensator experience loss of heat as a result of gas thermal conductivity. As such, at step 610, the example method determines whether the resistance value of the detector and the resistance value of the compensator are the same. If they are the same, the detector is poisoned.

In some embodiments, subsequent to step 610, the example method proceeds to step 612, where poisoning of the gas sensing apparatus is identified based on the comparison of detector resistance values with the compensator resistance values. Identifying poisoning of the detector may include determining that the detector generates no detection or catalytic reaction to gas while resistance values of the detector and resistance values of the compensator both indicate decreases, e.g., both detector and compensator are experiencing loss of heat from gas thermal conductivity. Additionally, an increase in electric current of the gas sensing apparatus may further indicate that both resistance values of the detector and the compensator are decreasing (e.g., due to imbalance of a bridge circuit of the gas sensing apparatus).

Poisoning of the gas sensing apparatus may also be identified by monitoring the resistance values of the compensator in relationship to the electric current of the gas sensing apparatus, or compensator resistance per wattage of power. Resistance value per power ratio may be used as a metric for determining detector functionality based on a circuit imbalance (e.g., of the bridge circuit) as a result of lower than normal resistance of detector. For example, a decrease in gas output detection due to partial poisoning can be detected by calculating a real-time resistance value per power ratio of the compensator and comparing it with a baseline/historical resistance value per power ratio of the compensator. A real-time resistance value per power ratio of the compensator that is lower than the baseline/historical resistance value per power ratio of the compensator may indicate partial positioning. In some embodiments, subsequent to step 612, the example method may return to step 602 and repeat the steps of example method 600 for a duration of time.

Referring to FIG. 7, the example method 700 may be executed by a computing device to test a gas sensing apparatus including a detector, a compensator, and a resistor (for example, as illustrated and described above in connection with at least FIG. 3). The detector may comprise a catalytic pellistor including a bead structure with catalytic material. The compensator may comprise a reference bead structure with non-catalytic material, and the resistance value of the compensator is matched with the resistance value of the detector.

At step 702, an initial resistor voltage value of a resistor is determined. The resistor may be configured on a gas sensing apparatus circuit of gas sensing apparatus for measuring electrical current of the circuit, similar to those described above. The initial resistor voltage value may be determined by receiving voltage measurement data from a measuring circuit configured to measure a voltage drop across the resistor.

In some embodiments, subsequent to step 702, the example method proceeds to step 704, where an initial detector voltage value of a detector and an initial compensator voltage value of a compensator are determined. The initial detector voltage value and the initial compensator voltage value may be determined by receiving voltage measurement data via measuring circuits coupled to the detector and the compensator, respectively. The initial detector voltage value and the initial compensator voltage value may be recorded and used as a baseline reference for establishing functionality of the detector and the compensator in the absence of a gaseous substance.

In some embodiments, subsequent to step 704, the example method proceeds to step 706, where an initial circuitry current value is calculated based at least in part on the initial resistor voltage value and a resistance value of the resistor. The resistor voltage value of the resistor may be used to determine the initial circuitry current value. The initial circuitry current value may comprise an amount of electrical current supplied to the gas sensing apparatus from a supply power source. The resistance value of the resistor may be a known or specific value such that the initial circuitry current value may be calculated based on the initial resistor voltage value and the resistance value of the resistor. For example, the initial resistor voltage value may be divided by the resistance value of the resistor to calculate the initial circuitry current value. The initial circuitry current value may then be used to calculate initial resistance values for various components of the gas sensing apparatus, such as the detector and the compensator, to measure functionality of the various components, which is discussed in further detail below.

In some embodiments, subsequent to step 706, the example method proceeds to step 708, where the computing device causes an injection of a gaseous substance to the gas sensing apparatus. The injection may comprise a controlled introduction of the gaseous substance to an environment configured with the gas sensing apparatus (e.g., an environment where the detector and the compensator of the gas sensing apparatus are positioned in). The time of injection may be recorded by the computing device to monitor for changes in voltage values of the detector and the compensator.

In some embodiments, subsequent to step 708, the example method proceeds to step 710, where a subsequent voltage value of the resistor, a subsequent compensator voltage value of the compensator and a subsequent detector voltage value of the detector are determined, similar to those described herein. The subsequent resistor voltage value, subsequent compensator voltage value, and the subsequent detector voltage value may correspond to change in voltages of the resistor, detector, and compensator a time after the injection of the gaseous substance to the gas sensing apparatus.

In some embodiments, subsequent to step 710, the example method proceeds to step 712, where a subsequent circuitry current value is calculated based on the subsequent voltage value of the resistor and the resistor value. Similar to calculating the initial circuitry current value as discussed above, the subsequent resistor voltage value may be divided by the resistance value of the resistor to calculate the subsequent circuitry current value. The subsequent circuitry current value may then be used to calculate subsequent resistance values for various components of the gas sensing apparatus, such as the detector and the compensator.

In some embodiments, subsequent to step 712, the example method proceeds to step 714, where changes in detector and compensator resistance values are calculated. Changes in resistance values may be calculated based at least in part on the initial circuitry current value, the subsequent circuitry value, the initial detector voltage value, the subsequent detector voltage value, the initial compensator voltage value, and the subsequent compensator voltage value.

For example, an initial detector resistance value may be calculated by dividing the initial detector voltage by the initial circuitry current value and a subsequent detector resistance value may be calculated by diving the subsequent detector voltage by the subsequent circuitry value. A difference between the initial detector resistance and the subsequent detector resistance may provide a change in detector resistance value. Similarly, an initial compensator resistance value may be calculated by dividing the initial compensator voltage by the initial circuitry current value and a subsequent compensator resistance value may be calculated by diving the subsequent compensator voltage by the subsequent circuitry value. A difference between the initial compensator resistance and the subsequent compensator resistance may provide a change in compensator resistance value.

Resistance change values of the detector and the compensator may be used in executing component failure analysis by the computing device. For example, a decrease in resistance of both detector and compensator may coincide with increased current draw from a finite voltage source, indicating a potential malfunction of at least the detector.

In some embodiments, subsequent to step 714, the example method proceeds to step 716, where a catalytic pellistor poisoning indicator is generated based at least in part on the compensator resistance change and the detector resistance change. The catalytic pellistor poisoning indicator may comprise an alarm or alert on a user interface of a gas monitoring system. In one embodiment, generating the catalytic pellistor poisoning indicator may comprise determining that the detector resistance change is analogous to the compensator resistance change subsequent to injection of the gaseous substance. According to another embodiment, generating the catalytic pellistor poisoning indicator may comprise determining decreasing detector resistance in conjunction with decreasing compensator resistance subsequent to injection of the gaseous substance.

As described above and as will be appreciated based on this disclosure, embodiments of the present disclosure may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Similarly, embodiments may take the form of a computer program code stored on at least one non-transitory computer-readable storage medium. Any suitable computer-readable storage medium may be utilized including non-transitory hard disks, CD-ROMs, flash memory, optical storage devices, or magnetic storage devices.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

The invention claimed is:

1. A method for detecting catalytic pellistor poisoning associated with a gas sensing device, the gas sensing device comprising a circuit including a resistor, a compensator, and a detector, the method comprising:
   determining, by a computing device, an initial resistor voltage value of the resistor, an initial compensator voltage value of the compensator, and an initial detector voltage value of the detector;
   calculating, by the computing device, an initial circuitry current value based on the initial resistor voltage value and a resistance value of the resistor;

subsequent to causing an injection of a gaseous substance to the gas sensing device:
  determining, by the computing device, a subsequent compensator voltage value of the compensator and a subsequent detector voltage value of the detector;
  calculating, by the computing device, a subsequent circuitry current value based on a subsequent resistor voltage value of the resistor and the resistance value;
  calculating, by the computing device, a compensator resistance change value based on the initial circuitry current value, the initial compensator voltage value, the subsequent circuitry current value, and the subsequent compensator voltage value;
  calculating, by the computing device, a detector resistance change value based on the initial circuitry current value, the initial detector voltage value, the subsequent circuitry current value, and the subsequent detector voltage value; and
  generating, by the computing device, a catalytic pellistor poisoning indicator based on a comparison between the compensator resistance change value and the detector resistance change value.

2. The method of claim 1, wherein the initial detector voltage value and the initial compensator voltage value comprises a baseline reference for establishing functionality of the detector and the compensator, respectively, wherein the baseline reference is associated with an absence of the gaseous substance.

3. The method of claim 1, wherein the initial circuitry current value comprises an amount of electrical current supplied to the circuit from a supply power source before the injection of the gaseous substance.

4. The method of claim 1, wherein calculating the initial circuitry current value further comprises dividing the initial resistor voltage value by the resistance value of the resistor.

5. The method of claim 1, further comprising:
  recording a time of the injection of the gaseous substance; and
  monitoring for changes in the subsequent compensator voltage value and the subsequent detector voltage value.

6. The method of claim 1, wherein the subsequent compensator voltage value and the subsequent detector voltage value correspond to a time after the injection of the gaseous substance.

7. The method of claim 1, further comprising executing component failure analysis using the compensator resistance change value and the detector resistance change value.

8. The method of claim 1, wherein generating the catalytic pellistor poisoning indicator comprises determining that the detector resistance change value is analogous to the compensator resistance change value subsequent to the injection of the gaseous substance.

9. The method of claim 1, wherein generating the catalytic pellistor poisoning indicator comprises determining decreasing detector resistance in conjunction with decreasing compensator resistance subsequent to the injection of the gaseous substance.

10. The method of claim 1, wherein the detector comprises a catalytic pellistor including a bead structure with catalytic material.

11. The method of claim 1, wherein the compensator comprises a reference bead structure with non-catalytic material.

12. A method, in a data processing system comprising a processor and a memory, for detecting catalytic pellistor poisoning of a gas sensing apparatus including a resistor, a detector, and a compensator, the method comprising:
  sampling, by the data processing system, a voltage reading of the resistor;
  calculating, by the data processing system, an electric current value of a gas sensing apparatus circuit based on the sampled voltage reading of the resistor;
  sampling, by the data processing system, voltage readings associated with the detector and the compensator for a duration of time;
  calculating, by the data processing system, one or more detector resistance values of the detector and one or more compensator resistance values of the compensator based on (i) the sampled voltage readings associated with the detector and the compensator and (ii) the electric current value;
  comparing, by the data processing system, the one or more detector resistance values with the one or more compensator resistance values; and
  identifying, by the data processing system, poisoning of the gas sensing apparatus based on the comparison of the one or more detector resistance values with the one or more compensator resistance values.

13. The method of claim 12 further comprising calculating the electric current value based on a resistance value associated with the resistor and the sampled voltage reading of the resistor.

14. The method of claim 13 further comprising calculating the electric current value by dividing the sampled voltage reading of the resistor by the resistance value of the resistor.

15. The method of claim 12, wherein the electric current value is provided to the detector and the compensator.

16. The method of claim 12, wherein the detector comprises a catalytic pellistor including a bead structure with catalytic material.

17. The method of claim 12, wherein the compensator comprises a reference bead structure with non-catalytic material.

18. The method of claim 12, wherein calculating the one or more detector resistance values and the one or more compensator resistance values further comprises dividing the sampled voltage readings associated with the detector and the compensator by the electric current value.

19. A system for detecting catalytic pellistor poisoning of a gas sensing apparatus including a resistor, a detector, and a compensator, the system comprising:
  a memory device having executable instructions stored therein; and
  a processor, in response to the executable instructions, configured to:
  sample a voltage reading of the resistor;
  calculate an electric current value of a gas sensing apparatus circuit based on the sampled voltage reading of the resistor;
  sample voltage readings associated with the detector and the compensator for a duration of time;
  calculate one or more detector resistance values of the detector and one or more compensator resistance values of the compensator based on (i) the sampled voltage readings associated with the detector and the compensator and (ii) the electric current value;
  compare the one or more detector resistance values with the one or more compensator resistance values, and
  identify poisoning of the gas sensing apparatus based on the comparison of the one or more detector resistance values with the one or more compensator resistance values.

* * * * *